United States Patent [19]
Dresden

[11] Patent Number: 5,964,758
[45] Date of Patent: Oct. 12, 1999

[54] LAPAROSCOPIC ELECTROSURGICAL INSTRUMENT

[76] Inventor: Scott Dresden, 10 Old Jackson Ave., #48, Hastings, N.Y. 10706

[21] Appl. No.: 08/933,020

[22] Filed: Sep. 18, 1997

[51] Int. Cl.⁶ .................................................. A61B 17/36
[52] U.S. Cl. ................................. 606/45; 606/51; 606/52
[58] Field of Search ........................ 606/41, 42, 45, 606/46, 48–52, 205–208

[56] References Cited

U.S. PATENT DOCUMENTS

| | | |
|---|---|---|
| 4,600,007 | 7/1986 | Lahodny et al. . |
| 4,655,216 | 4/1987 | Tischer . |
| 4,669,470 | 6/1987 | Brandfield . |
| 5,089,007 | 2/1992 | Kirsh et al. . |
| 5,258,006 | 11/1993 | Rydell et al. . |
| 5,330,471 | 7/1994 | Eggers . |
| 5,342,381 | 8/1994 | Tidemand . |
| 5,352,222 | 10/1994 | Rydell . |
| 5,352,235 | 10/1994 | Koros et al. . |
| 5,356,408 | 10/1994 | Rydell . |
| 5,445,638 | 8/1995 | Rydell et al. . |
| 5,456,684 | 10/1995 | Schmidt et al. . |
| 5,458,598 | 10/1995 | Feinberg et al. . |
| 5,462,546 | 10/1995 | Rydell . |
| 5,496,317 | 3/1996 | Goble et al. . |
| 5,514,134 | 5/1996 | Rydell et al. . |
| 5,527,313 | 6/1996 | Scott et al. . |
| 5,540,685 | 7/1996 | Parins et al. . |
| 5,569,243 | 10/1996 | Kortenback et al. . |
| 5,571,100 | 11/1996 | Goble et al. . |
| 5,573,535 | 11/1996 | Viklund . |

*Primary Examiner*—Michael Peffley
*Attorney, Agent, or Firm*—Joseph C. Mason; Dennis G. LaPointe; Mason & Associates, P.A.

[57] ABSTRACT

A laparoscopic electrosurgical instrument which has the capability to grasp, fulgurate, and cut tissue. The laparoscopic electrosurgical instrument has an electrically insulative longitudinal body having a proximal and distal end, and a housing at the distal end. A pair of grasping conductors extend longitudinally from the housing, the conductors being spaced apart in substantially parallel actuatable relationship, and each of the conductors also has a slot therein. A pair of scissors-like cutting members also extends from the housing from between the pair of conductors, and each of the cutting members has a proximal and distal end, with the proximal ends each pivotally connected to the housing and each distal end extending laterally through one of the slots of the pair of conductors. The proximal ends of the cutting member are in actuatable relationship to each other. There is also means extending through the longitudinal body for actuating the pair of conductors and pair of scissors-like cutting members, and for selectively supplying an electrical charge to the pair of conductors. On the proximal end of the body, there are means for controlling the actuation of the pair of conductors and pair of scissors-like cutting members.

9 Claims, 3 Drawing Sheets

LAPAROSCOPIC ELECTROSURGICAL INSTRUMENT

BACKGROUND OF THE INVENTION

1. Field of the Invention

The present invention relates generally to laparoscopic electrosurgical instruments. More particularly, the present invention relates to laparoscopic electrosurgical instruments which perform fulguration and have a pair of grasping conductors and a pair of scissors-like cutting members.

2. Description of the Related Art

The prior art as is best known to the inventor are laparoscopic surgical instruments which either have bipolar scissors-like cutting members at their distal ends, or have bipolar conductors at their distal end and have a single cutting blade therebetween. U.S. Pat. Nos. 4,655,216 to Tisher; 5,445,638 to Rydell, et al.; 5,458,598 to Feinberg, et al.; and 5,573,535 to Viklund, all demonstrate the feature of grasping bipolar conductors and a single cutting blade on the distal end of a laparoscopic surgical instrument. However, the single cutting blade lacks precision as it pushes tissue significantly prior to actual shearing.

Other devices in the art, such as U.S. Pat. No. 5,352,222 to Rydell, are simply bipolar surgical scissors which can carry current through the blades of the scissors to cauterize blood vessels in tissues. However, these devices lack the additional grasping function of conductors.

None of the prior art devices known to the inventor solve the problems addressed by the present invention, namely maintaining hemostasis through cauterization of blood vessels during laparoscopic procedures, while having the benefit of the precise cutting ability of scissors.

SUMMARY OF THE INVENTION

The present invention is a laparoscopic electrosurgical instrument comprised of an electrically insulative longitudinal body having a proximal and distal end, and a housing at the distal end; a pair of grasping conductors extending longitudinally from the housing, the conductors being spaced apart in substantially parallel actuatable relationship, and each of the conductors having a slot therein; a pair of scissors-like cutting members extending from the housing from between the pair of conductors, and each of the cutting members having a proximal and distal end, with the proximal ends each pivotally connected to the housing and each distal end extending laterally through one of the slots of the pair of conductors, the proximal ends of the cutting member being in actuatable relationship to each other; means extending through the longitudinal body for actuating the pair of conductors and pair of scissors-like cutting members; means for selectively supplying an electrical charge to the pair of conductors; and means at the proximal end of the body for controlling the actuation of the pair of conductors and pair of scissors-like cutting members.

The delivery of electrosurgical energy by a laparoscopic instrument is advantageous during dissection or parting of tissue as hidden blood vessels are easily ruptured and can be cauterized. It is further advantageous to have the same instrument performing the laparoscopic procedure able to cauterize as the blood vessels rupture as time is not required to switch instruments, thereby maintaining hemostasis.

Accordingly, the primary object of the present invention is to provide a single laparoscopic electrosurgical instrument which can grasp, fulgurate and precisely cut tissue, thereby maintaining hemostasis during the process of cutting and extirpating tissue.

It is another object of the present invention to provide a laparoscopic electrosurgical instrument which has actuatable scissors-like cutting members disposed between a pair of grasping conductors which fulgurate, as the cutting members can precisely grasp and cut tissue instead of pushing the tissue.

The above and yet further objects and advantages of the present invention will become apparent from the hereinafter set forth Brief Description of the Drawings and Detailed Description of the Invention.

DETAILED DESCRIPTION OF THE INVENTION

Figure 1:
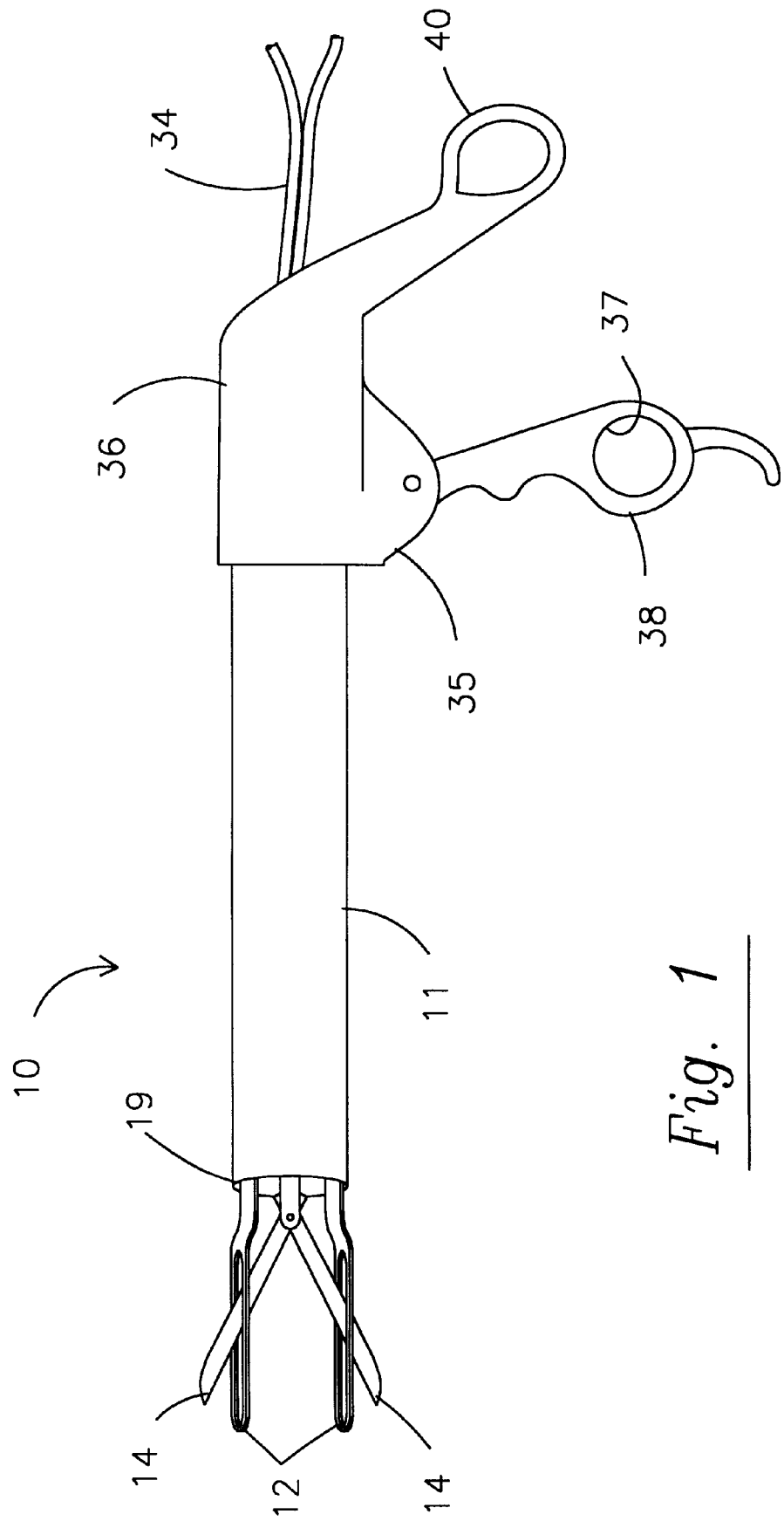
FIG. 1 is a side view of the present invention.

As illustrated in FIG. 1, the laparoscopic surgical instrument 10 is comprised of a longitudinal body 11, having a proximal end 36 a distal end 19. The longitudinal body can be shaped and dimensioned according to the desired use of the surgical instrument. For example, if use in endoscopy is desired, then the diameter of the body will be greatly narrowed. The only parameter governing the size of the diameter is the requirement that actuating means, be it mechanical or electrical, and electrical supply means 34 are able to fit through the length of the body from the means controlling actuation 35 to the pair of conductors 12 and pair of scissors-like cutting means 14.

The longitudinal body 11 is preferably made from a non-conductive, non-corrosive and biostatic material such that any current carried through the body 11 through the electrical supply means 34 to the pair of conductors 12 will not pass through outer surface of the body 11. Further, the longitudinal body could be rigid or semi-rigid depending on the type of surgery intended.

Figure 2:
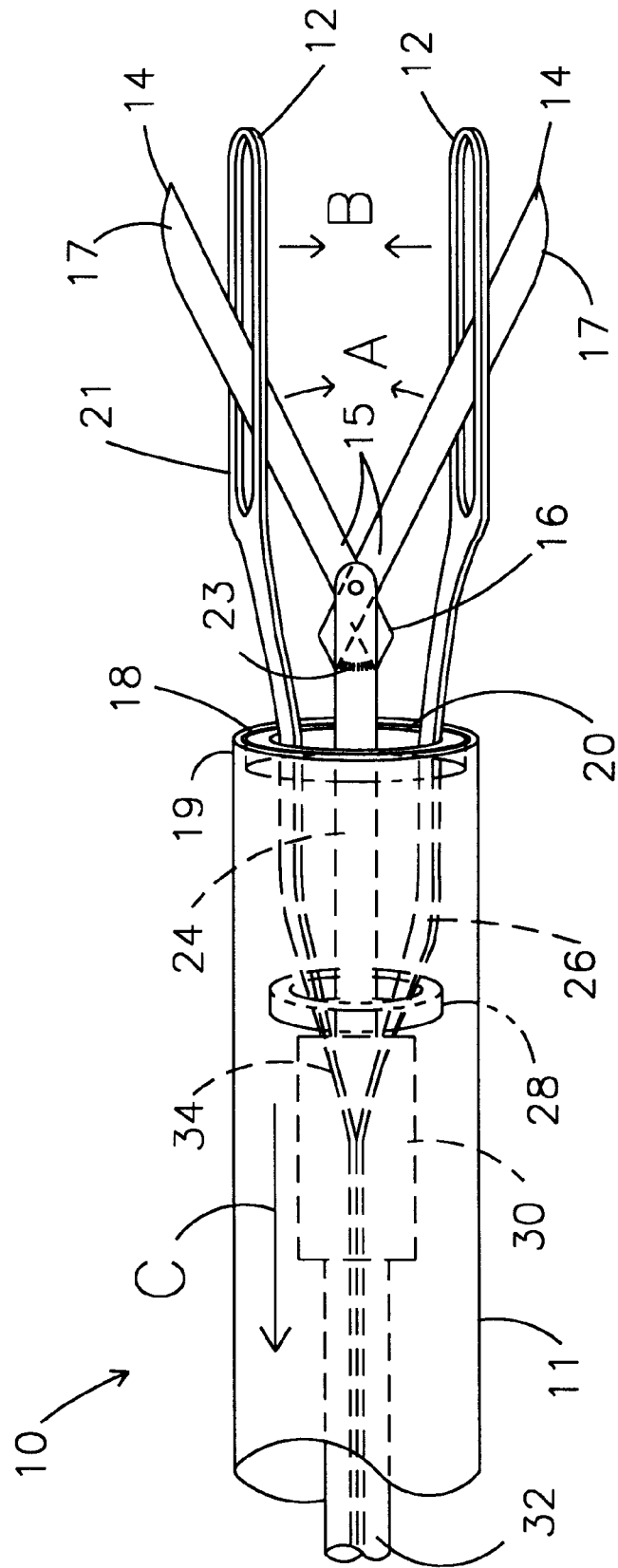
FIG. 2 is perspective view of the pair of grasping conductors and pair of scissors-like cutting members of the present invention.

As is shown in FIG. 2, on the distal end 19 of the longitudinal body 11 is a housing 18 from which longitudinally extends a pair of grasping conductors 12 for grasping and cauterization, and a pair of scissors-like cutting members 14 between the conductors 12. As used herein, "scissors-like" is resembling a pair of scissors in having opposed cutting members which are drawn together to cut whatever is between the cutting members in a shearing action.

The pair of grasping conductors 12 should be made from a conductive, non-corrosive, and biostatic material, such that they will not adversely interact with the fluids or tissues of the body when carrying an electrical current. The pair of grasping conductors 12 are rigidly attached at 30 to actuating means 32 within the housing 18 and longitudinal body 11. The actuating means 32 is shown here as a rod extending through the longitudinal body 11. Further, electrical supply means 34, also conductively touches the pair of conductors 12 in bipolar fashion, such that an electrical current may be carried through the conductors 12 to cauterize tissue and maintain hemostasis through a laparoscopic procedure.

The pair of grasping conductors 12 are in a substantially parallel arrangement, and are actuatable towards each other, as demonstrated by direction B; hence, the conductors 12 perform a "grasping" motion. The pair of grasping conductors 12 each have a slot 21 running through their length. The slot 21 is positioned to allow the distal ends 17 of the scissors-like cutting members 14 to pass through unobstructed. The pair of grasping conductors 12 can be shaped such that each conductor is the jaw of a forcep, which is advantageous for grasping and holding tissue.

The pair of scissors-like cutting members 14 are pivotally attached to each other at their respective proximal ends 15, and their proximal ends 15 include slight extensions 16 above and below actuating member 24 for the scissors-like cutting members 14. There is urging means 23 between the proximal ends of the pair of scissors-like cutting members 14 constantly urging the distal ends 17 of the scissors-like cutting members 14 open and between the slots 21 of the pair of conductors 12. Here, the urging means 23 is a spring. The pair of scissors-like cutting members 14 are shaped such that their closure creates a shearing action upon tissue between the cutting members.

The distal ends 17 of the pair of scissors-like cutting members 14 are preferably rounded to minimize damage to the tissue when the instrument is maneuvered between layers of tissue. Further, the cutting members 14 should be made from a rigid material to allow satisfactory shearing action, yet should not be conductive, or should be insulated to prevent shorting out the electrical supply means 34 if the cutting members 14 should contact the pair of grasping conductors 12.

The pair of grasping conductors 12 have ends 26 tapering to the connection with the actuating means 32. There is optionally a fixed first constricting ring 28 within the longitudinal body 11 about the tapering ends 26 of the pair of conductors 12 such that selectably urging the actuating means 32 towards the proximal end 36, shown as direction C, causes the tapering ends 26 to move towards each other, thereby causing the pair of conductors 12 to move towards each other in direction B, which allows the pair of conductors 12 to grasp. However, the tapering end 26 could be located at the housing 18, in which case the first constricting ring 28 within the longitudinal body 11 is not necessary as the housing 18 would perform the first constricting ring's function. Likewise, proximal retraction in direction C of the actuating means 32 causes the extensions 16 of the proximal ends 15 of the scissors-like cutting members 14 to abut second constricting ring 20 within the housing 18 of the distal end 19. This abutting creates pressure on the proximal ends 15 which causes the proximal ends 15 to move contra to the urging means 23 thereby effectuating the closure of the distal ends 17 of the scissors-like cutting members 14, shown as direction A. The pair of grasping conductors 12 coapts the tissue and moves proximally when closing, as embodied, in accord with the actuating means 32. This causes grasped tissue to be urged toward and pulled into the scissors-like cutting members 14.

Consequently, as embodied herein, the proximal retraction (direction C) of the actuating means 32 causes both the pair of conductors 12 and the pair of scissors-like cutting members 14 to close. However, if one desires the respective closing actions to be separately actuatable, then the use of two actuating means (not shown) would be appropriate. Such modification would necessarily cause a change in the control means 35 of the actuating means 32, which is discussed below.

Other mechanical linkage may be used for the actuating means 32, such as a cable or gearing. It is also possible to use electric motors and actuators as the means for actuating the pair of grasping conductors 12 and scissors-like cutting members 14.

Figure 3:
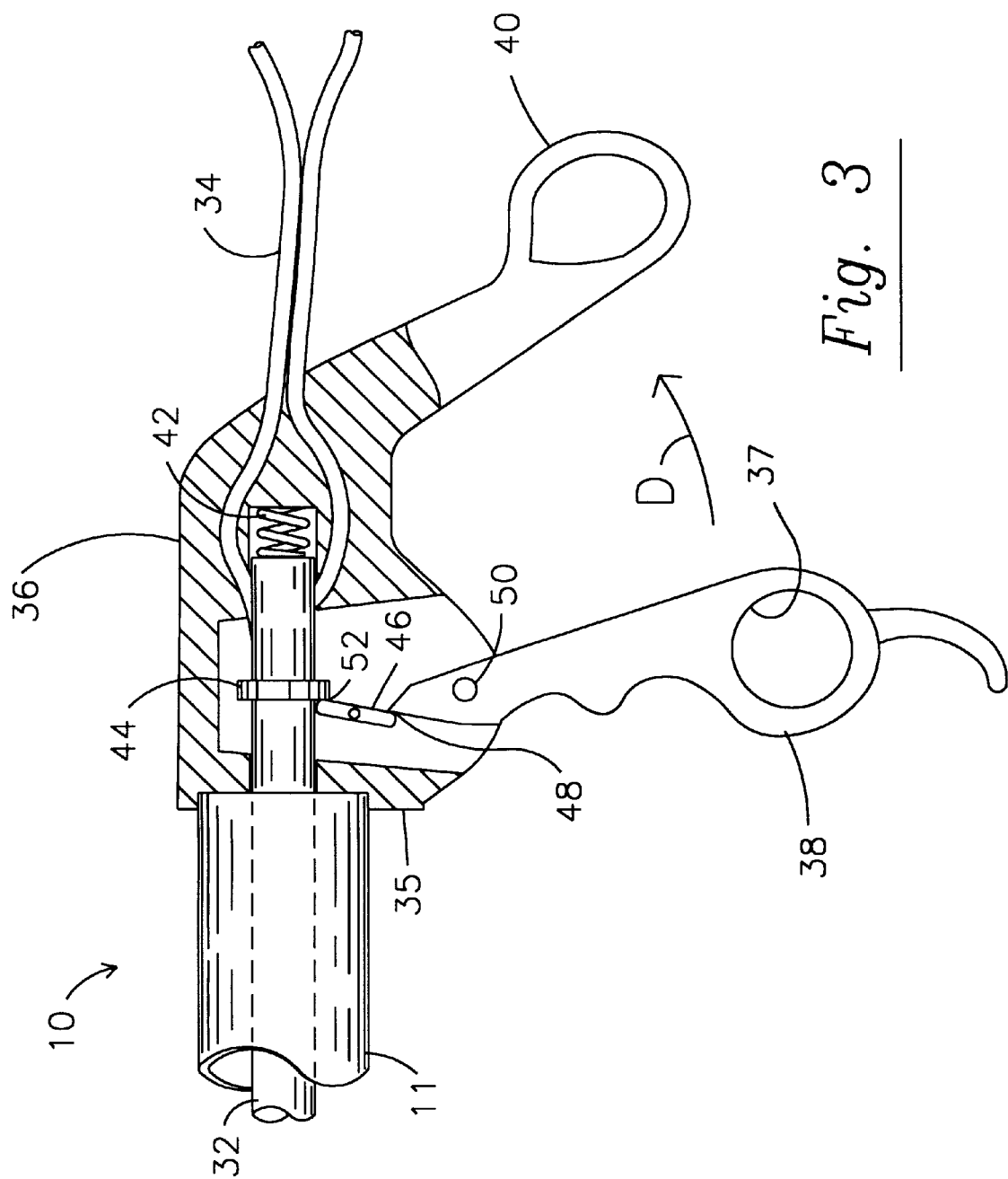
FIG. 3 is a side perspective view of the control means of the present invention.

The control means 35 for controlling the actuating means 32 is particularly shown in FIG. 3 as a "single trigger" mechanical handle. There is a stationary handle which includes a first fingerhold 40. There is also a movable member 38, having a second fingerhold 37, and the movable member 38 is pivotally mounted at pivot point 50 on the control means 35. The upper tip 48 of the moveable member 38 interacts with a lever 46 that is pivotally attached to the control means 35. The lever 46 also interacts at point 52 with a baffle 44 on the actuating means 32.

Upon proximal movement of the moveable member 38 in direction D, i.e. pulling on the fingerhold 37 of the moveable member 38, distal movement of the tip 48 is caused which interacts with the lever 46 and causes the lever to pivot and direct proximal force at point 52 on the baffle 44 and thereby causes the actuating means 32 to move proximally, in direction C as shown in FIG. 2.

The control means 35 also includes urging means 42, shown here as a spring, behind the actuating means 32 such that the actuating means 32 is constantly urged distally, and therefore, the pair of conductors 12 and pair of scissors-like cutting members 14 are constantly urged into the open position, such that the pair of conductors 12 are apart and the distal ends 17 of the pair of scissors-like cutting members 14 are extended between the slots 21 of the conductors 12. Only force exerted along direction D will cause the pair of conductors 12 and pair of scissors-like cutting members 14 to close, and remain closed until such force is removed. This allows only purposeful shearing by the cutting members 14 and grasping by the conductors 12 from actuation of the movable member 38.

If independent actuation of the pair of conductors 12 and the pair of scissors-like cutting members 14 is desired, then a second moveable member can be added to form a "double trigger" control means. A second actuating means (not shown) would be required to separately actuate the pair of grasping conductors 12 and the pair of scissors-like cutting members 14. Selective proximal force on the additional moveable member would then cause independent closure of either the pair of grasping conductors 12 or the scissors-like cutting members 14. Such embodiment is particularly useful when separate grasping and cauterization of tissue is desired.

The control means 35 further has electrical supply means 34, shown here as a dual wire from an external power source which enters the control means 35 and ultimately enters the actuating means 32, shown at 54. The wires extend through the length of the longitudinal body 11 and then each respectively connects to a conductor, as shown in FIG. 2, such that a current may be carried between the conductors to cauterize tissue. Alternatively, the scissors-like cutting members 14 may be attached (not shown) to the electrical supply means 34 such that a current passes from the cutting members acting as one pole to the pair of grasping conductors 12 acting as the other pole, thereby cauterizing tissue. The electrical supply may be turned on or off and manipulated externally to the laparoscopic electrosurgical instrument 10, as here, or the control means 35 may include electric supply control means in relation to effectuating cauterization by the pair of conductors 12.

While there has been shown a preferred and alternate embodiments of the present invention, it is to be understood that certain changes may be made in the form and arrangement of the elements of the invention without departing from the underlying spirit of the invention as particularly set forth in Claims.

What is claimed is:

1. A laparoscopic electrosurgical instrument, comprising:
   (a) an electrically insulative longitudinal body having a proximal and distal end;
   (b) a housing at the distal end of the body;
   (c) a pair of grasping conductors extending longitudinally from the housing, the conductors substantially parallel in spaced-apart actuatable relationship, each of the conductors having a slot therein;
   (d) a pair of scissors-like cutting members extending from the housing between the pair of conductors, each of the cutting members having a proximal and distal end, the proximal ends each being pivotally connected to the housing and the distal ends each extending laterally through one of the slots of the pair of conductors, the proximal ends further being in actuatable relationship to each other;
   (e) means extending through the longitudinal body for actuating the pair of conductors and the pair of scissors-like cutting members;
   (f) means extending through the longitudinal body for supplying an electrical charge to the pair of conductors; and
   (g) means at the proximal end of the longitudinal body for controlling the actuation of the pair of conductors and the pair of scissors-like cutting members.

2. The laparoscopic electrosurgical instrument as recited in claim 1, wherein the distal ends of the scissors-like cutting members are rounded to minimize trauma to tissue.

3. The laparoscopic electrosurgical instrument according to claim 2, wherein the scissors-like cutting members are designed to shear when being closed.

4. The laparoscopic electrosurgical instrument according to claim 3, wherein the scissors-like cutting members are made of non-conductive material.

5. The laparoscopic electrosurgical instrument according to claim 1, wherein the means for actuating the pair of conductors and the pair of scissors-like cutting members is a mechanical linkage with the means for controlling actuation.

6. The laparoscopic electrosurgical instrument as according to claim 5, wherein the means for controlling actuation is a single trigger.

7. The laparoscopic electrosurgical instrument according to claim 5, wherein the pair of conductors are each a jaw of a forcep.

8. A laparoscopic electrosurgical instrument, comprising:
   (a) an electrically insulative longitudinal body having a proximal and distal end;
   (b) a housing at the distal end of the body;
   (c) a pair of grasping conductors extending longitudinally from the housing, the conductors substantially parallel in spaced-apart actuatable relationship, each of the conductors having a slot therein, each of the conductors being shaped like a jaw of a forcep;
   (d) a pair of non-conductive scissors-like cutting members extending from the housing between the pair of conductors, each of the cutting members having a proximal and distal end, the proximal ends each being pivotally connected to the housing, and the distal ends each being rounded and extending laterally through one of the slots of the pair of conductors, the proximal ends further being in actuatable relationship to each other;
   (e) mechanical means extending through the longitudinal body for independently actuating the pair of conductors and the pair of scissors-like cutting members;
   (f) a wire extending through the longitudinal body for supplying an electrical charge to the pair of conductors; and
   (g) mechanical means at the proximal end of the longitudinal body for controlling the independent actuation of the pair of conductors and the pair of scissors-like cutting members.

9. The laparoscopic electrosurgical instrument according to claim 8, wherein the means for controlling independent actuation is a double trigger.

* * * * *